(12) United States Patent
DiFoggio

(10) Patent No.: US 7,516,655 B2
(45) Date of Patent: Apr. 14, 2009

(54) DOWNHOLE FLUID CHARACTERIZATION BASED ON CHANGES IN ACOUSTIC PROPERTIES WITH PRESSURE

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 279 days.

(21) Appl. No.: 11/393,770

(22) Filed: Mar. 30, 2006

(65) Prior Publication Data
US 2007/0227241 A1    Oct. 4, 2007

(51) Int. Cl.
*G01V 1/40*    (2006.01)
*G01N 29/00*    (2006.01)

(52) U.S. Cl. .................................. 73/152.58; 73/64.53

(58) Field of Classification Search .............. 73/152.02, 73/152.51, 152.53, 152.58, 152.52, 152.23, 73/64.53, 152.22, 152.32
See application file for complete search history.

(56) References Cited

U.S. PATENT DOCUMENTS

| | | | | | |
|---|---|---|---|---|---|
| 5,159,843 | A | * | 11/1992 | Shakkottai et al. | 73/24.05 |
| 5,741,962 | A | * | 4/1998 | Birchak et al. | 73/152.16 |
| 5,932,793 | A | * | 8/1999 | Dayton et al. | 73/24.05 |
| 6,065,328 | A | * | 5/2000 | Dayton et al. | 73/25.01 |
| 6,209,387 | B1 | * | 4/2001 | Savidge | 73/24.05 |
| 6,490,916 | B1 | * | 12/2002 | Goodwin et al. | 73/152.58 |
| 6,672,163 | B2 | * | 1/2004 | Han et al. | 73/597 |
| 6,758,090 | B2 | * | 7/2004 | Bostrom et al. | 73/152.58 |
| 6,763,698 | B2 | | 7/2004 | Greenwood | 73/30.01 |
| 6,813,962 | B2 | * | 11/2004 | Gysling et al. | 73/861.26 |
| 6,860,136 | B1 | * | 3/2005 | Hay et al. | 73/1.01 |
| 6,957,700 | B2 | | 10/2005 | Mandal | 166/250.01 |
| 6,971,259 | B2 | * | 12/2005 | Gysling | 73/32 A |
| 7,062,958 | B2 | * | 6/2006 | Diakonov et al. | 73/152.23 |
| 2003/0033866 | A1 | * | 2/2003 | Diakonov et al. | 73/152.55 |
| 2003/0164038 | A1 | * | 9/2003 | Han et al. | 73/152.58 |
| 2005/0173111 | A1 | | 8/2005 | Bostick, III | |
| 2005/0204808 | A1 | | 9/2005 | DiFoggio | 73/152.58 |
| 2005/0223808 | A1 | * | 10/2005 | Myers et al. | 73/629 |
| 2005/0224229 | A1 | | 10/2005 | Blacklaw | |
| 2006/0191683 | A1 | | 8/2006 | Fukuhara et al. | |

OTHER PUBLICATIONS

"Thermodynamic Models", http://home.olemiss.edu/~cmpcs/4213.html 4 pages.

Chandra M. Sehgal. "Non-Linear ultrasonics to determine molecular properties of pure liquids". Ultrasonics 1995 vol. 33. No. 2. pp. 155-161.

Uribe, et al. "Thermodynamic Properties of Gases and Liquids Determined from the Speed of Sound". Department of Chemical Engineering, Imperial College, London SW7 2BY, U.K.

(Continued)

*Primary Examiner*—Hezron E. Williams
*Assistant Examiner*—John Fitzgerald
(74) *Attorney, Agent, or Firm*—Cantor Colburn LLP

(57) ABSTRACT

Techniques for evaluating physical aspects of a formation fluid from within a wellbore include changing pressure on a sample of the formation fluid and transmitting at least one acoustic pulse through the fluid sample and analyzing acoustic information collected. Apparatus and methods for the evaluating involve using at least one acoustic transducer. Analyzing typically involves use of formulae that relate the fluid's equation of state and other properties to a change in the sound speed in the fluid as a function of pressure.

19 Claims, 4 Drawing Sheets

OTHER PUBLICATIONS

Oakley, et al. "Cv Ultrasonic Parameters as a Function of Absolute Hydrostatic Pressure. I. A Review of the Data for Organic Liquids". J. Phys. Chem. Ref. Data, vol. 32, No. 3, 2003. pp. 1-33.

Deiters, et al. "Guidelines for Publication of Equations of State-I. Pure Fluids". International Union of Pure and Applied Chemistry. Pure & Appl. Chem., vol. 69, No. 6. pp. 1237-1248, 1997.

* cited by examiner

DOWNHOLE FLUID CHARACTERIZATION BASED ON CHANGES IN ACOUSTIC PROPERTIES WITH PRESSURE

BACKGROUND OF THE INVENTION

1. Field of the Invention

The invention relates to geological exploration techniques, and more specifically to estimation of fluid properties from acoustic data.

2. Description of the Related Art

In various industrial processes that involve fluid material, it is useful to know the properties of the fluids involved. These properties include, for example, density, compressibility and acoustic impedance. In many applications, such as oil exploration and production, fluid properties are of particular interest. Reservoir engineers need to know the equation of state (EOS) for downhole fluids, especially hydrocarbon fluids, to decide the optimum way to produce a reservoir. An equation of state is a thermodynamic equation that relates a fluid's pressure, volume, and temperature. The simplest equation of state is the well-known equation, PV=nRT, for an ideal gas. However, the ideal gas equation is not useful downhole because, at downhole pressures and temperatures, even pure methane gas is far from being an ideal gas. The equations of state for liquids are much more complicated and often semi-empirical. There are "PVT" laboratories, which specialize in performing pressure, volume, and temperature analyses on recovered hydrocarbon fluid samples.

Attempts to correlate various physical properties of fluids to acoustic measurements are known. However, none of these other downhole acoustic methods make acoustic measurements at a plurality of pressures or attempt to determine a fluid's EOS or its EOS parameters (virial coefficients) to estimate fluid properties. For example, in U.S. Pat. No. 6,957,700, issued Oct. 25, 2005 and entitled "Self-Calibrated Ultrasonic Method of In-Situ Measurement of Borehole Fluid Acoustic Properties", tools and methods are disclosed that determine the acoustic impedance of drilling fluid using reflections from a precise metal disk. It does not describe making acoustic measurements while the fluid pressure is changing to determine an EOS or other fluid properties.

An example, which does not describe downhole use, is provided in U.S. Pat. No. 6,763,698, issued Jul. 20, 2004 and entitled "Self Calibrating System and Technique for Ultrasonic Determination of Fluid Properties." In this patent, a system and technique for determining fluid properties includes an ultrasonic transducer on a first surface of a solid member. A longitudinal ultrasonic pulse is delivered through the solid member and a multiplicity of pulse echoes caused by reflections of the ultrasonic pulse between the solid-fluid interface and the transducer-solid interface are detected and processed. The speed of ultrasound in the fluid is determined and the fluid density is determined as a function of the speed of ultrasound and the determined acoustic property. It does not describe making acoustic measurements while the fluid pressure is changing in order to determine an EOS or other fluid properties.

Comprehensive analysis of subsurface samples is frequently completed at a surface PVT laboratory after the sample tanks are withdrawn from a wellbore. Given that sampling may occur at depths where the environment is at a comparatively high temperature and pressure, it is recognized that the delicate balance exists for dissolved components within a retained sample. That is why a sample may be changed quite substantially by the mere act of withdrawal to the surface (where temperatures and pressure are substantially lower). Asphaltenes and waxes may precipitate out of solution and it could take weeks of agitation in the lab at high temperature and pressure (an arduous task called "recombination") to get those components back into solution. Accordingly, various sampling techniques have included certain protocols to overcome such problems and preserve sample integrity. One such technique involves overpressuring a sample (typically by several thousand psi above formation pressure) within a sample chamber to limit or prevent separation into two phases or precipitation of certain components within the sample as the sample shrinks from cooling during its return to the surface. However, when possible, it is still preferable, to make these fluid property measurements in situ as described in the present invention. Making the measurement downhole insures that the fluid sample is in a relatively pristine state. Also, for any single run of the tool there are a limited number of sample tanks that can deployed. To test the fluids from more zones in the well than one has sample tanks requires making a downhole measurement or making a return trip into the well with the tool.

Present techniques for using acoustic signals to determine or estimate physical and chemical properties of a sample taken in the wellbore fail to provide for certain desired in-situ analyses of subsurface samples. More specifically, present techniques that employ acoustic signals for sample analysis do not make acoustic measurements at a plurality of pressures. Also, they do not use the change in acoustic properties with pressure to estimate an EOS or other fluid properties.

It is known that applying pressure to a fluid will change its acoustic properties and that one can glean additional fluid property information from how rapidly these acoustic properties change with pressure. For example, reference may be had to a journal article entitled "Non-linear Ultrasonics to Determine Molecular Properties of Pure Liquids," Sehgal, C. M., Ultrasonics Vol. 33, No. 2, 1995, pp 155-161. This article states that wave propagation through condensed media is fundamentally non-linear, and presents several relationships between fluid properties and the rate of change in the speed of sound with pressure.

What is needed is a technique to evaluate a formation fluid sample in situ that provides some of the analyses previously only available from a surface PVT lab.

SUMMARY OF THE INVENTION

Disclosed is an apparatus for evaluating a fluid sample, including a tool adapted for insertion into a wellbore and receiving the fluid sample into a sample chamber, the sample chamber adapted for changing a pressure of the fluid sample and having at least one acoustic transducer coupled to the sample chamber, the acoustic transducer for evaluating the fluid sample in a pressurized state with at least one acoustic signal.

Also disclosed is a method for evaluating properties of a fluid sample, the method for disposing a tool into a wellbore; receiving the fluid sample into a sample chamber of the tool; changing a pressure of the fluid sample; transmitting at least one acoustic signal into the fluid sample; and analyzing the at least one acoustic signal to evaluate the properties of the fluid sample.

Further disclosed is a computer program product stored on machine readable media, the product including instructions for evaluating properties of a fluid sample in a downhole environment, by changing a pressure of the fluid sample within a sample chamber; transmitting at least one acoustic signal into the fluid sample; and analyzing the at least one acoustic signal to evaluate the properties of the fluid sample.

Examples of certain features of the invention have been summarized here rather broadly in order that the detailed description thereof that follows may be better understood and in order that the contributions they represent to the art may be appreciated. There are, of course, additional features of the invention that will be described hereinafter and which will form the subject of the claims appended hereto.

BRIEF DESCRIPTION OF THE DRAWINGS

For detailed understanding of the present invention, references should be made to the following Detailed Description of the Invention, taken in conjunction with the accompanying drawings, in which like elements have been given like numerals, wherein.

The detailed description explains the preferred embodiments of the invention, together with advantages and features, by way of example with reference to the drawings.

DETAILED DESCRIPTION OF THE INVENTION

Figure 1:
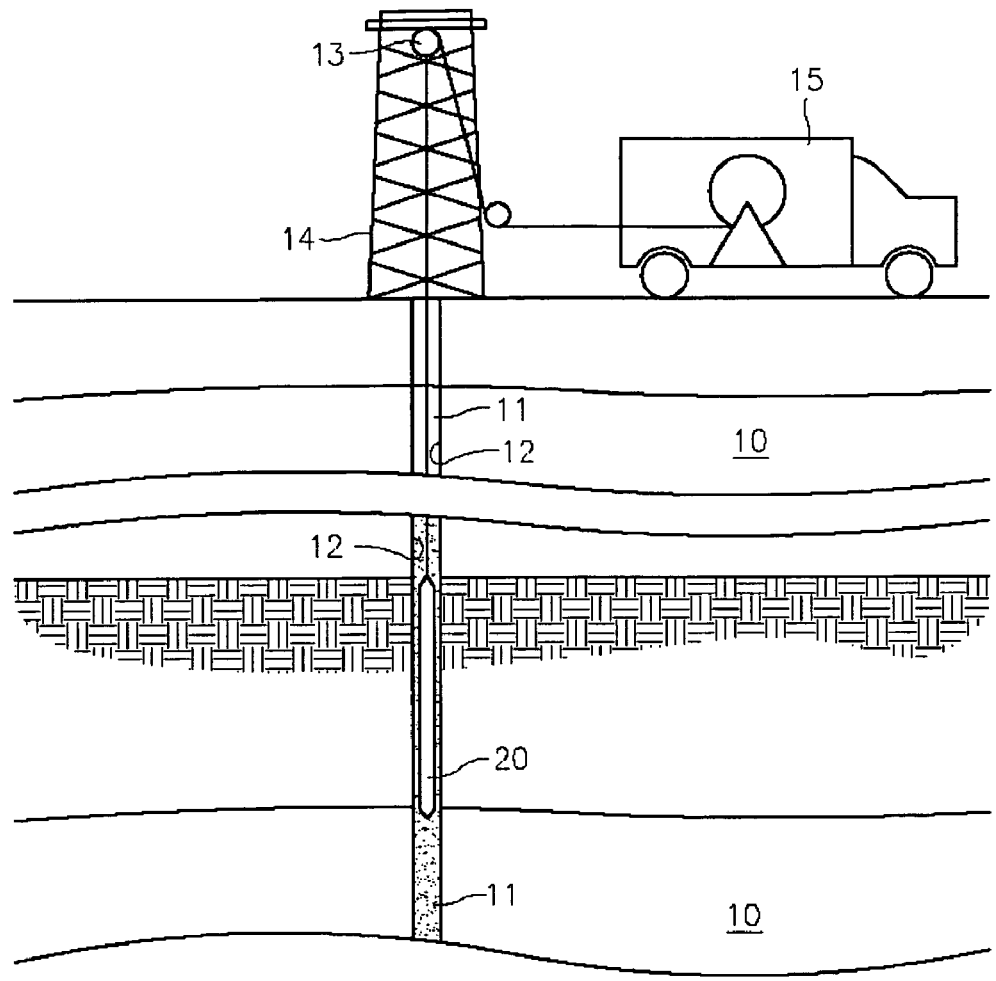
FIG. 1 depicts aspects of subsurface sampling in a wellbore.

Turning now to FIG. 1, a cross-section of earth formations 10 along the length of a penetration referred to as a "wellbore" 11 is depicted. Usually, the wellbore 11 is at least partially filled with a mixture of liquids including water, drilling fluid, mud, oil and formation fluids that are indigenous to the formations 10 penetrated by the wellbore 11. Suspended within the wellbore 11 at the bottom end of a wireline 12 is a formation fluid sampling tool 20. The wireline 12 is often carried over a pulley 13 supported by a derrick 14. Wireline 12 deployment and retrieval is typically performed by a powered winch carried by a service truck 15.

Figure 2:
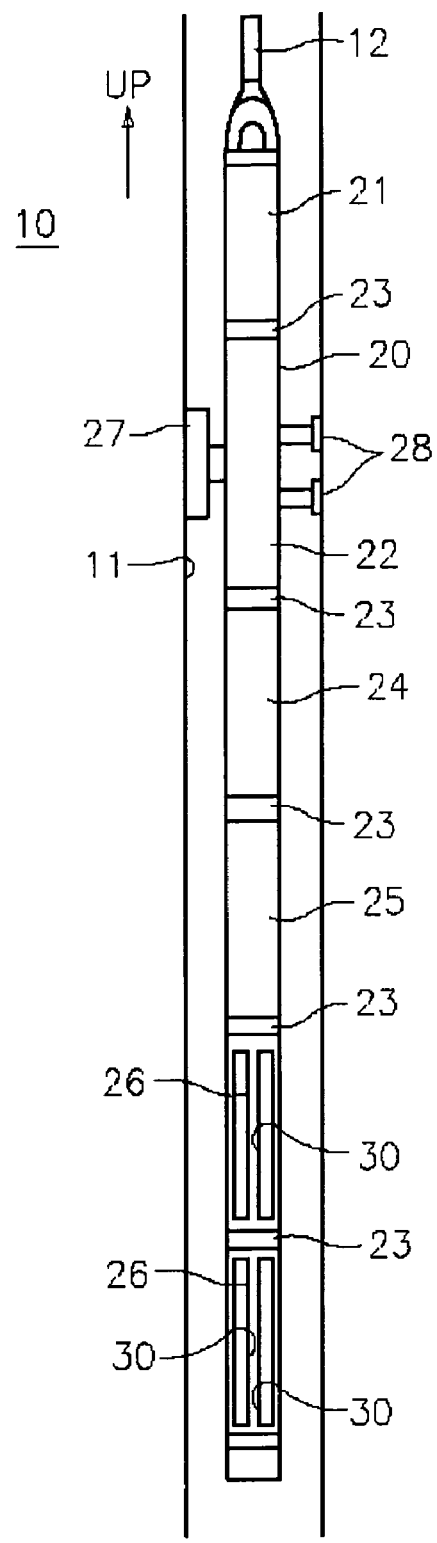
FIG. 2 depicts aspects of a sampling tool within the wellbore.

An exemplary embodiment of the sampling tool 20 is schematically illustrated by FIG. 2. In this non-limiting embodiment, the sampling tool 20 includes an assembly of several tool segments that are joined end-to-end by the threaded sleeves or mutual compression unions 23. The assembly of tool segments include a hydraulic power unit 21 and a formation fluid extractor 22. Below the extractor 22, a large volume pump 24 is provided for line purging. Below the large volume pump 24 is a similar small volume pump 25 having a smaller displacement volume than the large volume pump 24. A plurality of sample tank magazine sections 26 is assembled below the small volume pump 25. Each magazine section 26 includes at least one sample tank 30 for retention of a fluid sample.

In this embodiment, the formation fluid extractor 22 includes an extensible "suction" probe 27, which reduces the pressure slightly below formation pressure to allow formation fluid to flow into the probe 27. The probe 27 is opposed by borehole wall backup arms 28. Both the suction probe 27 and the backup arms 28 are hydraulically extensible to firmly engage the walls of the wellbore 11.

In some embodiments, at least one of the large volume pump 24, the small volume pump 25 and remote a supply of pressurized gas (not shown) provide pressure behind a piston enclosing the formation fluid sample in the at least one sample tank 30 when commanded. The pressure is typically called for once a sample has been collected and disposed within the sample tank 30. This gas cushion is much more compressible that the typical formation fluid so pressure of the formation fluid does not change as much with falling temperature as does the pressure of a liquid. In a container filled only with liquid, when the liquid shrinks slightly from falling temperatures, the pressure that the liquid exerts on its confining container drops dramatically. That is why a gas cushion is often used to maintain the liquid sample under pressure and in a single phase as the sample chamber is brought to the surface. A piston separates the gas cushion from any other fluids that are within the sample tank.

The teachings herein provide for use of at least one acoustic transducer in cooperation with the sampling tool 20. The at least one transducer provides for determination of acoustic properties of a sample, at a plurality of pressures, typically near the formation pressure. Determination of the acoustic properties provides for deriving other fluid properties from it's the measured acoustic properties. As techniques for pressurizing the sample tank 30 or other components of the sampling tool 20 are known, these aspects of sample handling are not generally discussed further herein.

Although the teachings herein make reference to use of a sampling tool 20, it should be recognized that the techniques disclosed herein are not limited to use with a sampling tool 20. For example, a variety of tools may be used for retrieving samples from a wellbore. For example, tools referred to as testing tools, survey tools, pressure tools and other such tools may be used in support of the teachings herein. Any one of these and other similar tools may be construed to be a "tool" as used herein. Accordingly, the term "sampling tool 20" is merely illustrative and not limiting of the teachings herein.

Techniques are also known for determining at least a sample density using acoustic pulse decay. Reference may be had to U.S. Patent Application No.: 2005/0204808 entitled "Method and Apparatus for an Acoustic Pulse Decay Density Determination" by the applicant herein, and incorporated herein by reference in its entirety.

Figure 3:
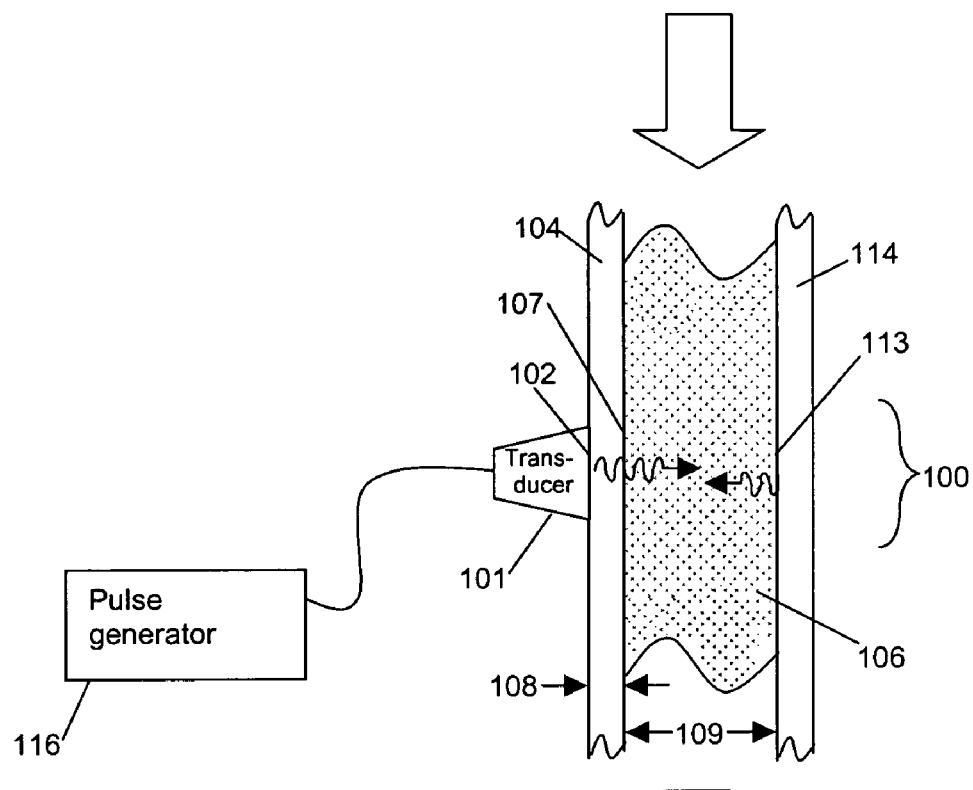
FIG. 3 depicts a flow line leading to a sample tank in which the sample may be overpressurized; and, FIG. 4 depicts a method for determining physical aspects of the sample.

Turning now to the exemplary embodiment depicted in FIG. 3, a sample line 40 that leads to the sample tank 30 is depicted. A direction of flow of a sample 106 in the sample line 40 is depicted by the arrows in FIG. 3. The sample line 40 is overpressurized and surrounds the sample 106 of formation fluid. A portion of the sample line 40 where sample analysis is performed is referred to, for convenience, as a "sample chamber 100." The term "sample chamber 100" as used herein refers to any place where the sample 106 is evaluated by applying the teachings herein. Accordingly, the sample line 40 is illustrative of one non-limiting embodiment of the sample chamber 100.

Although the formation fluid that is ultimately retained in the tool 20 typically includes substantially more fluid than the portion depicted in the sample chamber 100, in this embodiment (and some others), the portion depicted in the sample chamber 100 is referred to as the sample 106. This is for convenience and not limiting of the teachings herein. As used herein, the term "sample 106" generally indicates the portion of retained formation fluid that is "evaluated" by, subjected to or interrogated with an acoustic signal.

In this non-limiting embodiment, the sample 106 is bounded by the sample chamber 100 that includes a near-wall 104 and a far-wall 114. Pressure may be increased on the sample 106 by compressing the formation fluid through movement of a pump piston (not shown), or through other techniques.

In typical the wellbore 11, the pressure of the formation fluid ranges from about 6,000 pounds per square inch (psi) to about 15,000 psi. It is recognized that in some instances, the formation fluid pressure can range from about 3,000 psi to about 30,000 psi, and possibly higher (or lower).

Typically, the sample 106 is overpressurized to pressures of several thousand pounds per square inch (psi) or more above formation fluid pressure. For example, the sample 106 may be overpressurized between about 500 pounds per square inch (psi) and about 3,500 psi, however, this range should be construed as merely illustrative and not limiting.

The terms "overpressure," "overpressurized" and other similar terms are generally to be construed in terms of sample pressure in relation to pressure in the sampling environment and the pressure of the formation fluid in the sampling environment. That is, it should be recognized that the formation fluid, when sampled, is typically at a pressure that is substantially greater than the atmospheric pressure. Overpressurizing the sample 106 typically means raising the pressure applied to the sample 106 to a degree that is at least slightly above formation pressure, and may be substantially above formation pressure.

Likewise, "underpressurizing" the sample 106 may be desired, in some instances. In such embodiments, underpressurizing the sample 106 calls for slightly relieving the pressure on the sample 106, and may call for substantially relieving up to completely relieving the pressure on the sample 106.

Therefore, the terms "changing" as well as "pressurizing" and other similar terms regarding sample pressure contemplate overpressurizing the sample 106 as well as underpressurizing the sample 106.

Accordingly, it should be recognized that the pressure on the sample 106 may be varied considerably to provide users with additional data regarding aspects of the properties of the sample 106.

In the embodiment of FIG. 3, an acoustic transducer 101 is coupled to the near-wall 104 of the sample line 40 at an acoustic interface 102. The acoustic transducer 101 communicates with a pulse generator 116. The pulse generator 116 typically includes electronics suitable for generating an acoustic signal (e.g., a "pulse") and for monitoring signals associated with the acoustic pulse. Typically, the wall thickness 108 of the sample line 40 and the internal width 109 of the sample line 40 are selected to enhance acoustic performance during sample analysis. During sample analysis, acoustic signals are transmitted from a near-wall/fluid interface 107 through the sample 106 and reflect off of a far-wall/fluid interface 113.

The acoustic transducer 101 produces at least one acoustic signal for evaluation of the sample 106. The at least one acoustic signal may be reflected, returned, directed or transmitted through the sample 106 in any manner useful for evaluation thereof. The acoustic signal is typically generated using a frequency that is selected for evaluation of downhole fluids. Although the acoustic signal may be selected by reference to properties of the sample 106, the sample chamber 100 and other properties, it should be recognized that acoustic transducers 101 that can be operated over a broad range of frequencies may be useful with the teachings herein.

More specifically, the transit time of an acoustic pulse through a known distance in a fluid is a common way to measure sound speed within a fluid. An acoustic pulse generally consists of one or more complete cycles of an acoustic wave. The main frequency of this acoustic wave can range anywhere from infrasound to audible sound to ultrasonic.

The preferred transit distance through fluid depends on the wavelength of sound within the fluid. The wavelength of sound is computed as the sound speed in the fluid divided by its frequency. To accurately determine the arrival time of an acoustic pulse and the corresponding transit time, it is preferable that the transit distance be much greater than the wavelength of sound because each acoustic pulse is generally spread out spatially over one or more wavelengths of that sound. Stated equivalently, the transit time is typically much longer than the pulse duration, which includes one or more complete cycles. Therefore, a larger sample chamber is used for low frequency sound when compared to the sample chamber used for measuring sound speed with high frequency sound.

Of course, one should recognize that the sample line 40 need not be a primary sample line. For example, the sample chamber 100 may be a secondary sample line to which a portion of the sample flow is diverted. Such embodiments may be desired, at least in some instances, for separately adjusting pressure on portions of the sample 106, for improving acoustic properties of the sample chamber 106, and for other reasons.

In one example, the acoustic transducer 101 includes a 10 MHz transducer 101. The sample chamber 100 is fabricated from a titanium alloy. In this embodiment, the internal width 109 of the sample chamber 100 is about 0.218" and the wall thickness 108 is about 0.110." Typically, acoustic surfaces of the sample chamber 100 (for example, the surface at the acoustic interface 102, the near-wall/fluid interface 107 and the far-wall/fluid interface 113) are planar and parallel to each other. In some embodiments, the sample chamber 100 includes a separate listening transducer (not shown) for monitoring the acoustic signal.

Typically, the pressure is elevated to a level such that the sample 106 remains in a state that is consistent with the ambient state of formation fluid in the sample environment. As temperatures and pressures in the downhole environment of the wellbore 11 can be relatively high, the sample chamber 100 is designed to accommodate substantial pressure (pressure that is well above the relatively high pressure in the formation). Accordingly, it is recognized that determinations of sample properties when the sample 106 is under extreme pressure requires accounting for the substantial pressure. The teachings herein provide for determinations of sample properties at least while the collected sample 106 is under a compensating pressure for maintaining the phase of the sampling state.

Some other embodiments for evaluation of the sample 106 involve using the sample tank 30 as the sample chamber 100. In these embodiments, the transducer 101 is placed in contact with a wall of the sample tank 30. The transducer provides for a plurality of measurements as the pressure inside the tank changes. One skilled in the art will recognize that the sample 106 may be subjected to various pressure levels during various stages of sampling and retrieval, and that evaluation of the sample 106 may be performed in a number of these stages. Accordingly, using the sample tank 30 as the sample chamber 100 is merely one embodiment for evaluation of aspects of the sample 106 and not limiting of the teachings herein.

In order to provide for determination of properties of the sample 106, relationships between acoustic signals and molecular properties are required. Exemplary equations are provided in a reference entitled "Non-Linear Ultrasonics to Determine Molecular Properties of Pure Liquids," Sehgal, C. M., Ultrasonics Vol. 33, No. 2, 1995, pp 155-161, which is incorporated herein by reference in its entirety.

As shown in Sehgal equations 1-3, an initial fluid pressure P and a pressurized fluid pressure P' can be related to an initial fluid density $\rho$ and a pressurized fluid density $\rho'$ by using $P'/P=(\rho'/\rho)^\xi$ where $\xi$ is a constant. Writing $\rho'=\rho+\Delta\rho$, this equation can be expanded as a Taylor series about the original density, $\rho$, so that $P'=P+\Sigma_{n=1}^{\infty}(n!)^{-1}(\partial^n P'/\partial \rho^n)[\rho'-\rho]^n$ where ($\partial^n P'/\partial \rho^n$) represents an n-th derivative of P' evaluated at $\rho$, while holding the entropy S constant. The term [$\rho'-\rho$] can be replaced by $\Delta\rho$. For a low compressibility fluid, the expansion typically need only be carried out to a couple of terms. We can further define $A=\rho(\partial P'/\partial \rho)$ and $B=\rho^2(\partial^2 P'/\partial \rho^2)$ to simplify the appearance of the resulting approximation equation.

Accordingly, physical properties of the sample 106 may be estimated using a generalized equation of state for the sample 106. An isentropic condition means that the entropy, S, is held constant. Mathematically, an isentropic condition is indicated by the subscript, S as shown in Equation 1. A virial equation that relates pressure P with density $\rho$ for an isentropic condition is:

$$P = P_o + A\left(\frac{\Delta\rho}{\rho}\right)_s + \frac{B}{2!}\left(\frac{\Delta\rho}{\rho}\right)_s^2; \tag{1}$$

where
P represents pressure;
$P_O$ represents initial pressure in the sample chamber 100;
$\rho$ represents a density of the sample 106;
$\Delta\rho$ represents a change in the density of the sample 106; and,
A, B represent virial coefficients.

The virial coefficients A, B define a pressure-density relationship for the sample 106. The ratio of these virial coefficients expressed:

$$\frac{B}{A} = \left(\frac{2\rho c}{(dc/dP)}\right); \tag{2}$$

where
dc/dP represents a derivative of sound speed c with respect to pressure, P;
c represents the speed of sound in the sample 106; and,
$\rho$ represents the density of the sample 106.

A change in the cohesive energy $\Delta A_c$ of the sample 106 may be described as:

$$\Delta A_c = -\left[\frac{M_c^2}{(B/A+1)}\right]\ln\left(\frac{82.051 T\rho}{M}\right); \tag{3}$$

where
$\Delta A_c$ represents the cohesive energy of the sample 106, typically expressed in ergs/gm;
$M_c$ represents an average molecular weight of the sample 106; and,
T represents a temperature of the sample 106.

Further, a solubility parameter, $\delta$, referred to as the "Hilderbrand parameter" is expressed as:

$$\delta = \sqrt{\left[\left(\frac{\rho c^2}{(B/A+1)}\right)\ln\left(\frac{V_g}{V_l}\right)\right]}; \tag{4}$$

where
$V_g$, $V_l$ represent a molar volume of the sample 106 in a gaseous state and a liquid state, respectively.

Although van der Waals constants may be best suited for estimation of physical properties related to gaseous media, the van der Waals constants a, b can be applied to liquid media. These constants can be determined by acoustic measurement of B/A and c and through application of the following equations:

$$a = \left[\frac{\rho c^2 V_l^2}{(B/A+1)}\right]; \text{ and} \tag{5}$$

$$b = V_l - \frac{RT}{\rho c^2}(B/A+1); \tag{6}$$

where
a represents a measure of attractive forces between molecules in the sample 106;
b is a relation to the size of the molecules in the sample 106; and,
R represents an ideal gas constant.

Figure 4:
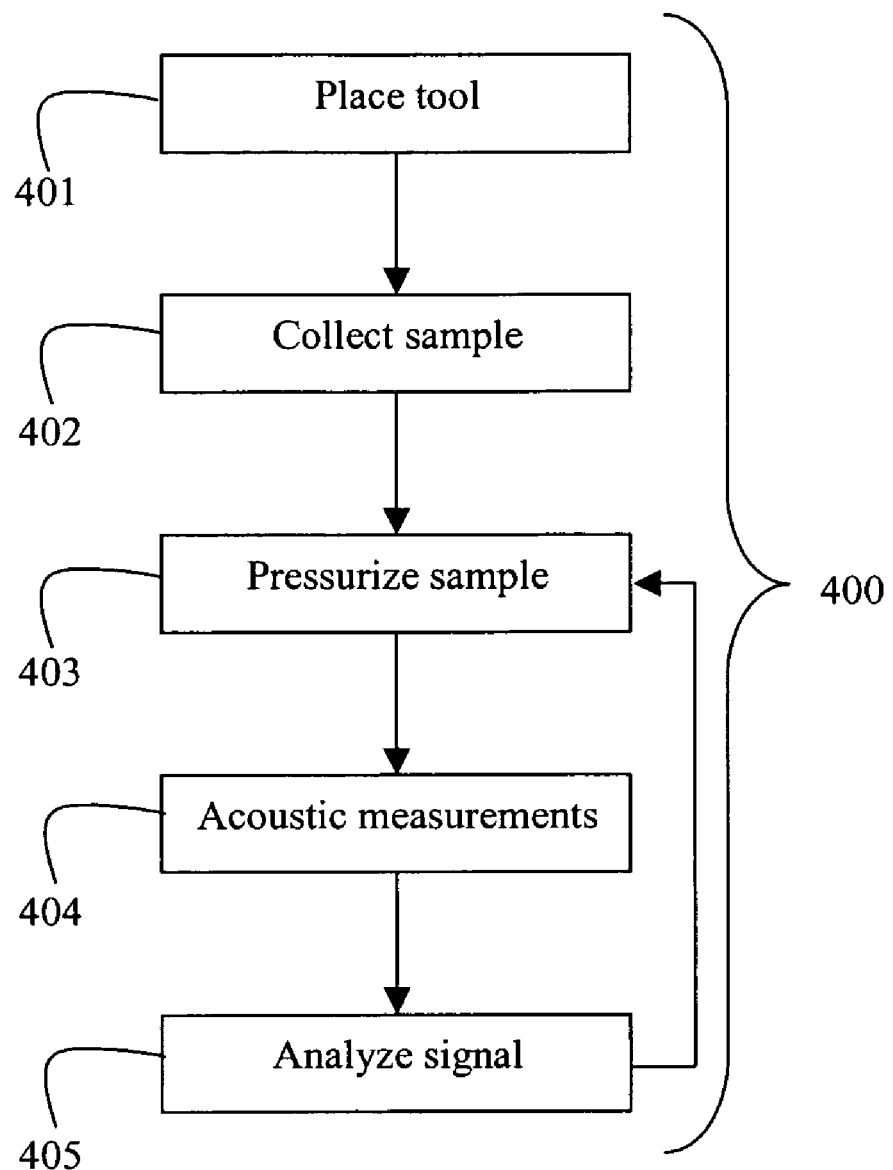

Referring now to FIG. 4, one non-limiting embodiment of a method for evaluating the sample 106 is provided. In FIG. 4, sample evaluating 400 involves placing the sampling tool 401 into the sampling environment; collecting the sample 402; pressurizing the sample 403 (typically above formation pressure); making at least one acoustic measurement 404 and analyzing the signal 405. Typically, acoustic measurement 404 is performed at a plurality of pressures, as indicated by the upward arrow in FIG. 4 indicating a repetition of the pressurizing, measuring and analyzing.

Placing the sampling tool 401 and collecting the sample 402 involve known techniques and do not warrant further discussion. Pressurizing the sample 403 also involves known techniques. However, it should be noted that, as alluded to above, pressurizing the sample 403 typically involves applying pressure to the fluid 106 throughout the flow path of the fluid in the sampling tool 20. Therefore, acoustic measurements 404 and analyzing of the signal 405 may be performed at other locations along the flow path of the sample 106 within the sampling tool 200.

Making acoustic measurements 404 is completed using known techniques for interrogating media with acoustic energy. These known techniques take advantage of exemplary components as depicted and discussed herein, and may involve other components not touched upon in this disclosure.

Analyzing the signal 405 may be completed using a variety of techniques. For example, reference may be had to U.S. Patent Application No. 2005/0204808, previously incorporated by reference. This reference patent application teaches, among other things, a method for estimating a property of a fluid, that includes transmitting a first acoustic pulse in a first member that is in contact with the fluid; detecting a plurality of acoustic pulse echo returns from an interface between the first member and the fluid; and estimating the property of the fluid from the plurality of acoustic pulse echo returns.

In the method for estimating, the property of the fluid includes at least one of acoustic impedance, density and viscosity of the fluid. A further step includes at least one of estimating a reflection coefficient of the interface between the first member and the fluid; estimating an acoustic impedance of the first member; and estimating a slope of energy decay for the plurality of acoustic pulse echo returns. In some embodiments, estimating the slope of energy decay includes performing a least squares fit to the plurality of acoustic pulse echo returns; in some other embodiments, estimating the slope of energy decay includes dividing each of the plurality of acoustic pulse echo returns into a plurality of time windows. In some further embodiments, estimating the slope of energy decay further includes integrating over each of the plurality of time windows; in other embodiments, estimating the slope of energy decay further includes subtracting noise from each of the plurality of acoustic pulse echo returns.

The method for estimating may further call for transmitting a second acoustic pulse through the fluid; and estimating speed of sound through the fluid, using round trip travel time for the second acoustic pulse between the first member and a second member that is in contact with the fluid.

Alternatively, the method for estimating may call for transmitting a second acoustic pulse through the fluid; and estimating attenuation of the second acoustic pulse through the fluid. In some embodiments, estimating the attenuation includes estimating the attenuation at a plurality of frequencies. In some embodiments, transmitting the second acoustic pulse further includes transmitting a plurality of acoustic pulses at a plurality of frequencies. In typical embodiments, the estimating is performed downhole.

In other embodiments, analyzing the signal 405 calls for evaluating acoustic signals according to the exemplary Eq. 1 though Eq. 6 disclosed herein. Of course, other relationships may be realized by one skilled in the art which provide for determination of physical aspects of the sample 106 by use of acoustic signals. It is considered that these other relationships are within the contemplation of the teachings herein, and accordingly within the scope of the appended claims.

One skilled in the art will also recognize that the sample evaluating 400 may include various other steps, combinations of steps, or omit certain steps. For example, in embodiments where the sample 106 is evaluated in the sample line, collecting the sample 402 and pressurizing the sample 403 may be essentially a single step.

In further embodiments, other sensors are used in addition to the acoustic transducer 101 for evaluation of the sample 106. For example, temperature of the sample 106 may be monitored with a temperature sensor (not shown). Various combinations of data from the various sensors may prove advantageous for evaluations of certain aspects of the sample 106, such as density ρ.

In some embodiments, it may be considered advantageous to undertake partially pressurizing the sample 403 (to, for example, a predetermined pressure) then undertake making acoustic measurements 404 and analyzing the signal 405 before continuing with pressurizing the sample 403. For example, it may be considered that embodiments using stepwise pressurizing and analyzing of the sample 106 provide users with additional data for use with further relationships for further characterization of the sample 106.

In support of the teachings herein, various computer components including software may be had to provide for operation and analyses of the apparatus and methods disclosed herein. Accordingly, it is considered that these teachings may be implemented as a set of computer executable instructions stored on a computer readable medium, comprising ROM, RAM, CD ROM, flash or any other computer readable medium, now known or unknown, that when executed cause a computer to implement the method of the present invention. These instructions may provide for equipment operation, control, data collection and analysis and other functions deemed relevant by a user.

While the foregoing disclosure is directed to the exemplary embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

What is claimed is:

1. A tool for evaluating a fluid downhole, comprising:
a sample chamber adapted for having the fluid disposed therein, a pump for providing fluid communication with the fluid;
a transducer for providing acoustic communication with the fluid; and
a processor in data communication with the transducer and the pump;
wherein the processor is adapted to change the pressure of the fluid, excite the transducer and receive acoustic data and compute a rate of change of sound speed in the fluid.

2. The tool as in claim 1, wherein the sample chamber comprises at least one of a sample tank and a sample line.

3. The tool as in claim 1, further comprising electronics coupled to the transducer for generating the acoustic communication.

4. The tool as in claim 1, further comprising electronics and a listening transducer coupled to the sample chamber for monitoring the acoustic communication.

5. The tool as in claim 1, wherein a pressure in the sample chamber comprises pressure of between about 500 pounds per square inch (psi) and about 3,500 psi above a formation fluid pressure.

6. The tool as in claim 1, wherein the sample comprises at least one of water, drilling fluid, mud, oil and formation fluids.

7. The tool as in claim 1, wherein a source of pressure for changing the pressure comprises at least one of the pump and a remote supply.

8. The tool as in claim 1, wherein the processor comprises a digital computer.

9. A method for evaluating a property of a fluid, comprising:
receiving the fluid into a sample chamber;
changing a pressure of the fluid sample;
transmitting at least one acoustic signal into the fluid sample; and
analyzing the at least one acoustic signal to evaluate the a rate of change of the sound speed in the fluid with pressure.

10. The method as in claim 9, wherein the changing, transmitting and analyzing are performed for a plurality of pressure levels.

11. The method as in claim 9, wherein the changing comprises at least one of substantially overpressurizing, overpressurizing, slightly overpressurizing, slightly underpressurizing, substantially underpressurizing, and completely relieving pressure.

12. The method as in claim 9, wherein changing the pressure comprises pressurizing to at least one predetermined pressure.

13. The method as in claim 9, wherein evaluating the properties of the fluid comprises solving the relationship:

$$P = P_0 + A\left(\frac{\Delta \rho}{\rho}\right)_s + \frac{B}{2!}\left(\frac{\Delta \rho}{\rho}\right)_s^2$$

where

P represents pressure applied to the fluid;
$P_0$ represents pressure in the sample chamber for an unpressurized state;
ρ represents a density of the fluid;
Δρ represents a change in the density of the fluid; and
A, B represent virial coefficients for the fluid.

14. The method as in claim 9, wherein evaluating the properties of the fluid comprises solving the relationship:

$$\frac{B}{A} = \left(\frac{2\rho c}{(dc/dP)}\right);$$

where
dc/dP represents a derivative of a speed of sound c with respect to pressure, P applied to the fluid;
c represents the speed of sound in the fluid;
ρ represents the density of the fluid; and
A, B represent virial coefficients for the fluid.

15. The method as in claim 9, wherein evaluating the properties of the fluid comprises solving the relationship:

$$\Delta A_c = -\left[\frac{M_c^2}{(B/A+1)}\right] \ln\left(\frac{82.051 T\rho}{M}\right);$$

where
$\Delta A_c$ represents a cohesive energy of the fluid;
$M_c$ represents an average molecular weight of the fluid;
T represents a temperature of the fluid;
ρ represents the density of the fluid; and
A, B represent virial coefficients for the fluid.

16. The method as in claim 9, wherein evaluating the properties of the fluid comprises solving the relationship:

$$\delta = \sqrt{\left[\left(\frac{\rho c^2}{(B/A+1)}\right) \ln\left(\frac{V_g}{V_l}\right)\right]};$$

where
δ represents a solubility parameter for the fluid;
$V_g, V_l$ represent a molar volume of the fluid for a gaseous state and a liquid state, respectively;
c represents the speed of sound in the fluid;
ρ represents the density of the fluid; and
A, B represent virial coefficients for the fluid.

17. The method as in claim 9, wherein evaluating the properties of the fluid comprises solving the relationship:

$$a = \left[\frac{\rho c^2 V_l^2}{(B/A+1)}\right];$$

where
α represents a measure of attractive forces between molecules in the fluid;
$V_1$ represents a molar volume of the fluid for a liquid state;
c represents the speed of sound in the fluid;
ρ represents the density of the fluid; and
A, B represent virial coefficients for the fluid.

18. The method as in claim 9, wherein evaluating the properties of the fluid comprises solving the relationship:

$$b = V_l - \frac{RT}{\rho c^2}(B/A+1);$$

where
b bears a relation to the size of the molecules in the fluid;
R represents an ideal gas constant;
$V_l$ represents a molar volume of the fluid for a liquid state;
c represents the speed of sound in the fluid;
ρ represents the density of the fluid; and
A, B represent virial coefficients for the fluid.

19. The method as in claim 9, wherein changing the pressure comprises maintaining the fluid in a liquid state.

\* \* \* \* \*